United States Patent
Cheng et al.

(10) Patent No.: US 9,090,655 B2
(45) Date of Patent: Jul. 28, 2015

(54) LOW HEMOLYTIC ANTIMICROBIAL PEPTIDE, PHARMACEUTICAL COMPOSITION AND USE THEREOF

(75) Inventors: Jya-Wei Cheng, Taichung (TW); Kuo-Chun Huang, Changhua (TW); His-Tsu Cheng, Hsinchu (TW); Hui-Yuan Yu, Taipei (TW)

(73) Assignee: RISE TECHNOLOGY CO., LTD., Apia (WS)

( * ) Notice: Subject to any disclaimer, the term of this patent is extended or adjusted under 35 U.S.C. 154(b) by 419 days.

(21) Appl. No.: 13/074,864

(22) Filed: Mar. 29, 2011

(65) Prior Publication Data
US 2011/0294724 A1 Dec. 1, 2011

(30) Foreign Application Priority Data
Mar. 29, 2010 (TW) ................ 99109396 A

(51) Int. Cl.
| | |
|---|---|
| *A61K 38/12* | (2006.01) |
| *C07K 7/08* | (2006.01) |
| *C07K 7/64* | (2006.01) |
| *A61P 33/02* | (2006.01) |
| *A61K 38/08* | (2006.01) |
| *A61P 31/04* | (2006.01) |
| *A61P 31/10* | (2006.01) |
| *A61P 31/12* | (2006.01) |
| *C07K 7/06* | (2006.01) |
| *A61K 38/10* | (2006.01) |
| *C07K 14/47* | (2006.01) |
| *A61K 38/00* | (2006.01) |

(52) U.S. Cl.
CPC ... *C07K 7/06* (2013.01); *C07K 7/08* (2013.01); *C07K 14/4723* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 2004/0072990 A1* | 4/2004 | Tzeng et al. | 530/317 |
| 2006/0166883 A1 | 7/2006 | Lu | 514/12 |
| 2007/0020624 A1* | 1/2007 | Rubenfield et al. | 435/6 |
| 2012/0189682 A1* | 7/2012 | O'Neil et al. | 424/411 |

OTHER PUBLICATIONS

Gordon and Romanowski ("A review of Antimicrobial Peptides and their therapeutic potential as anti-infective drugs", Current Eye Research (2005), vol. 30;pp. 505-515).*
Ma ("Animal Models of Disease", Modern Drug Discover, Jun. 2004, p. 30-36).*
Jorgensen et al. ("Recent trends in stabilizing peptides and proteins in pharmaceutical formulation-considerations in the choice of excipients", Expert Opinion Drug Delivery. (2009) vol. 6 (11); pp. 1219-1230).*
UniProt C0C2S0_CLOT (Entered UniProt May 5, 2009).
Benkovic (Cell Cycle 4:4, 552-555: Apr. 2005).
Akers et al. (Guide to Microbial Control in Pharmaceutical and Medical devices: Chp. 17 Official Methods of Preservative Evaluation and Testing, 2007).

* cited by examiner

*Primary Examiner* — James H Alstrum Acevedo
*Assistant Examiner* — Tara Martinez
(74) *Attorney, Agent, or Firm* — WPAT, P.C.; Anthony King; Kay Young

(57) ABSTRACT

Disclosed is an antimicrobial peptide having an amino acid sequence of formula presented as $(P_1)_M(nA_1X_1X_2)_N(P_2)_X$, wherein $P_1$ is selected from the group consisting of basic amino acids including Arg and Lys; $A_1$ is selected from the group consisting of aromatic amino acids including Trp, Phe and Ala; $X_1$ is selected from the group consisting of basic amino acids or nonpolar amino acids, including Arg, Lys, Val, Leu, Ala and Ile; $X_2$ is selected from the group consisting of basic amino acids or nonpolar amino acids, including Arg, Lys, Val, Leu, Ala and Ile; $P_2$ is selected from the group consisting of basic amino acids including Arg and Lys; and the numbers of M and X are respectively 0~2; when N>2, $A_1$ is Ala and the Ala residues are less than N−2.

11 Claims, 1 Drawing Sheet

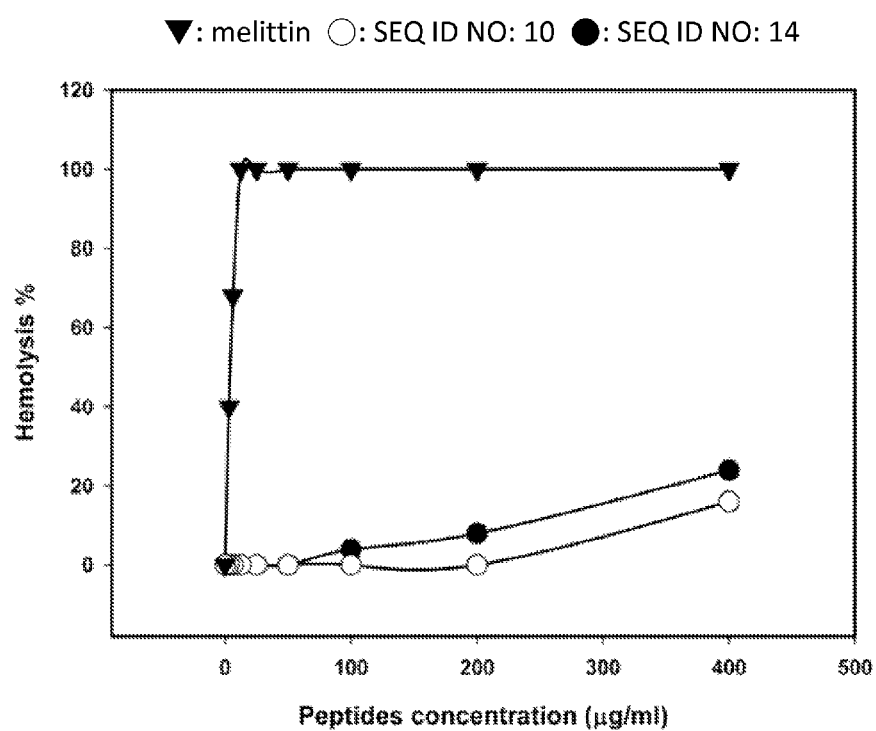

LOW HEMOLYTIC ANTIMICROBIAL PEPTIDE, PHARMACEUTICAL COMPOSITION AND USE THEREOF

CROSS-REFERENCE TO RELATED APPLICATIONS

This Non-provisional application claims priority under 35 U.S.C. §119(a) on Patent Application No(s). 099109396 filed in Taiwan, Republic of China Mar. 29, 2010 the entire contents of which are hereby incorporated by reference.

FIELD OF THE INVENTION

The present invention relates to an antimicrobial peptide, and particularly relates to a low hemolytic antimicrobial peptide, pharmaceutical composition and use thereof.

BACKGROUND OF THE INVENTION

The emergence of bacterial strains that are resistant to conventional antibiotics has prompted a search for new therapeutic agents, including antimicrobial peptides of animal origin. Antimicrobial peptides have been recognized as playing an important role in the innate host defense mechanisms of most living organisms including those of plants, insects, amphibians and mammals, and are known to possess potent antibiotic activity against bacteria, fungi, and certain viruses. The antimicrobial peptides readily partition into phospholipid bilayers with greater than 95% of the peptides binding to lipid to compromise membrane integrity. In bacteria, antimicrobial peptides are able to cause small, transient increases in conductance in planar lipid bilayers, thereby partially depolarizing the cytoplasmic membrane potential gradient.

The protective function of antimicrobial peptides in innate host defense mechanisms has been demonstrated in *Drosophila*, where reduced expression of such peptides dramatically decreases survival rates after microbial challenge. In mammals, a similar function is suggested by defective bacterial killing in the lungs of cystic fibrosis patients and in small mice.

The antimicrobial peptides found in mammals may be classified into the cysteine-rich defensins ($\alpha$- and $\beta$-defensin) and various groups within the cathelicidin family. Based on the amino acid composition and structure, the cathelicidin family may be classified into three groups. The first group includes the amphipathic $\alpha$-helical peptides such as LL-37, CRAMP, SMAP-29, PMAP-37, BMAP-27, and BMAP-28. The second group contains the Arg/Pro-rich or Trp-rich peptides including Bac5, Bac7, PR-39, and indolicidin. The third group includes Cys-containing peptides such as protegrins. Cathelicidin families contain a highly-conserved signal sequence and proregion known as the cathelin domain and a variable antimicrobial sequence in the C-terminal domain. Many cathelicidins contain a characteristic elastase cleavage site between the anionic cathelin domain and the cationic C-terminal peptide domain. Proteolytic processing at this site has been observed in bovine and porcine neutrophils and is required for microbicidal activity. Although these antimicrobial peptides have a broad spectrum of activity against many microbial organisms, they may have different hemolytic activities for erythrocytes, so that their pharmaceutical potential is restricted. Therefore, the low hemolytic antimicrobial peptides are disclosed in the present invention, they have not only the outstanding antimicrobial activities but also have low hemolytic activities as well.

As antimicrobial peptides are low molecular mass molecules of less than 5 kDa possessing broad-spectrum activity and constituting an important part of the host defense against microbial infections, they provide a starting point for designing low molecular mass antibiotic compounds. Furthermore, they are known to have a propensity to fold into amphipathic structures with clusters of hydrophobic and charge regions, a feature contributing to their membranolytic activity. Despite these antimicrobial peptides having a broad spectrum of activity against many microbial organisms, they may have different hemolytic activities for erythrocytes, so that their pharmaceutical potential is restricted.

SUMMARY OF THE INVENTION

It is an object of the present invention to provide a low hemolytic antimicrobial peptide, composition and use thereof.

In one embodiment of the present invention, the antimicrobial peptide of the present invention has an amino acid sequence of formula presented as $(P_1)_M(nA_1X_1X_2)_N(P_2)_X$. $P_1$ may be a basic amino acid such as Arg and Lys; $A_1$ may be an aromatic amino acids such as Trp, Phe and Ala. $X_1$ may be a basic amino acid or nonpolar amino acid such as Arg, Lys, Val, Leu, Ala or Ile. $X_2$ may be a basic amino acid or nonpolar amino acid such as Arg, Lys, Val, Leu, Ala or Ile. $P_2$ may be a basic amino acid such as Arg and Lys. The subscripts M may have values from 0-2 inclusive; subscript X has a value from 0-2 inclusive; and N has a value from 2-4 inclusive. The compound may also contain Ala residues. When N>2 $A_1$ is Ala, and Ala residues are less than N minus 2 (meaning that if N is equal to three, then the number of Ala is equal to one).

By modifications of primary and secondary structures, the peptides can be obtained and some of their important features can be also analyzed, so as to improve the activity or toxicity of nature antimicrobial peptides. The antimicrobial peptides of the present invention are novel and tryptophan-rich peptides. The peptides have outstanding antimicrobial and low hemolytic activity so that they are suitable for manufacture of antibiotics, and can be used to broadly resist gram-positive bacteria, gram-negative bacteria, protozoa, fungi or Human immunodeficiency virus (HIV).

In another embodiment of the present invention, the antimicrobial peptide is selected from the group consisting of SEQ ID NO: 1 to 7, has linear or cyclic conformation, and can be further modified by acetylation, amidation, formylation, hydroxylation, lipid modification, methylation or phosphorylation.

The peptides of the present invention may improve the activity or toxicity of natural antimicrobial peptides. In the future, the peptides can be used to manufacture antibiotics, pharmaceutical composition or for other clinical antimicrobial uses. Through their outstanding antimicrobial effect and low hemolytic activity, these peptides may broadly resist microorganisms such as gram-positive bacteria, gram-negative bacteria, protozoa, fungi or viruses.

In yet another embodiment of the present invention, the antimicrobial peptide of the present invention and pharmaceutically acceptable carrier can be used to manufacture pharmaceutical composition as antimicrobial agent. The carrier is an excipient, diluent, thickening agent, bulking agent, binder, disintegrating agent, lubricant, oil-based/non-oil-based agent, surfactant, suspending agent, gelling agent, adjuvant, preservative agent, anti-oxidant, stabilizing agent, coloring agent, or flavoring agent. The dosage form of the pharmaceutical composition is an embedding, dip, infusion, patch, powder, tablet, injection, suspension, external aqueous solution, drop, liniment, inhalant, embrocation, paste, lotion, cream, ointment, or gel. The composition can be administered to mammals by means of oral, subcutaneous, injective or inhalation administration.

The embodiments of the present invention are further described through below detailed examples and the drawings.

BRIEF DESCRIPTION OF THE DRAWINGS

FIG. 1 shows hemolytic activities of Pem-2252, Pem-2254, and melittin.

DETAILED DESCRIPTION

Embodiment 1

Design, Synthesis, Purification and Characterization of Peptides

The antimicrobial peptides of the present invention are listed as table 1, the amino acid residues are presented by 3-letter abbreviation.

mixed in different ratios using gradient elution. The wavelength for detection was set at 225 nm and 280 nm, and the flow rate for elution was 4 ml/min. The major peptide products were characterized by fast atom bombard mass spectrophotometry to determine the molecular weight of each peptide. The purity of each peptide was analyzed by RP-HPLC.

Embodiment 2

Determination of Peptide Activity In Vitro

The in vitro antimicrobial activities of antimicrobial agents were tested using minimum inhibition concentration (MIC) tests. The MIC value is the lowest concentration of peptide at which the visible growth of test organisms was inhibited and reduced. The test strains herein were *E. coli* (ATCC 25922), *Pseudomonas aeruginosa* (ATCC 27853) and *Staphylococcus aureus* (ATCC 29213).

Overnight cultures of the test organisms were diluted to produce an inoculum containing approximately $10^5$ colonies in Meuller-Hinton broth (MHB). Peptide solution with different concentrations was added to diluted culture of the test organisms. After 18 hours of incubation at 37° C., the results were assayed for turbidity as an indicator of cell growth. MIC

TABLE 1

| name | amino acid sequence | ID NO |
|---|---|---|
| Pem-1001 C | Lys Phe Lys Arg Trp Leu Ala | SEQ ID NO: 1 |
| Pem-1001 L | Lys Phe Lys Arg Trp Leu Ala | SEQ ID NO: 2 |
| Pem-1002 C | Lys Phe Arg Ala Trp Val Arg | SEQ ID NO: 3 |
| Pem-1002 L | Lys Phe Arg Ala Trp Val Arg | SEQ ID NO: 4 |
| Pem-1003 C | Lys Trp Lys Ile Trp Leu Lys | SEQ ID NO: 5 |
| Pem-1003 L | Lys Trp Lys Ile Trp Leu Lys | SEQ ID NO: 6 |
| Pem-2251 C | Lys Lys Trp Arg Ala Trp Leu Lys Trp Leu Ala Lys Lys | SEQ ID NO: 7 |
| Pem-2251 L | Lys Lys Trp Arg Ala Trp Leu Lys Trp Leu Ala Lys Lys | SEQ ID NO: 8 |
| Pem-2252 C | Lys Lys Trp Arg Lys Trp Leu Arg Ala Ile Ala Lys Lys | SEQ ID NO: 9 |
| Pem-2252 L | Lys Lys Trp Arg Lys Trp Leu Arg Ala Ile Ala Lys Lys | SEQ ID NO: 10 |
| Pem-2253 C | Lys Lys Phe Arg Arg Phe Val Arg Phe Ile Ala Lys Lys | SEQ ID NO: 11 |
| Pem-2253 L | Lys Lys Phe Arg Arg Phe Val Arg Phe Ile Ala Lys Lys | SEQ ID NO: 12 |
| Pem-2254 C | Lys Lys Trp Arg Lys Trp Leu Lys Trp Leu Ala Lys Lys | SEQ ID NO: 13 |
| Pem-2254 L | Lys Lys Trp Arg Lys Trp Leu Lys Trp Leu Ala Lys Lys | SEQ ID NO: 14 |

Note:
C denote cyclic topology and L denote linear topology

All of the cyclic and linear peptides herein were synthesized by solid-phase peptide synthesis using the standard Fmoc (N-(9-fluoroenyl)methoxycarbonyl) protocol manually on PAL resin (5-(4-Fmoc-aminomethyl-3,5-dimethoxyphenoxy-valeric acid-MBHA). Fmoc protective groups of the resin were removed by 20% piperidine/DMF for 1-1.5 hr and checked by ninhydrin test. 95% TFA was added and mixed for 1-1.5 hr to obtain the crude peptides. The crude peptides were then analyzed and purified by reverse phase high pressure liquid chromatography (RP-HPLC) using a Vydac C18 reversed-phase column. The mobile phase for elution was a mixture of acetonitrile and deionized $H_2O$ values for the peptides were measured three times at different time points. The mean MIC values are shown in Table 2. According to the results, Pem-2251 L and Pem-2254 L showed the better antimicrobial activity against *E. coli, Pseudomonas aeruginosa* and *Staphylococcus aureus*. In particular, the MIC values of Pem-2254 L were 1.565, 1.565 and 3.125 (µg/ml) for *E. coli, Pseudomonas aeruginosa* and *Staphylococcus aureus*, respectively. On the other hand, modifications for primary or secondary structures without influencing their activity, such as acetylation, amidation, formylation, hydroxylation, lipid modification, methylation or phosphorylation, were performed herein. The peptide activity in vitro was then tested and also exhibited their antimicrobial activity.

TABLE 2

| | MIC (µg/ml) | | |
|---|---|---|---|
| peptide name | E. coli (ATCC 25922) | P. aeruginosa (ATCC 27853) | S. aureus (ATCC 29213) |
| Pem-1001 C | >50 | >50 | >50 |
| Pem-1001 L | 50 | 50 | 50 |
| Pem-1002 C | >50 | >50 | >50 |
| Pem-1003 L | 25 | 12.5 | 12.5 |
| Pem-2251 C | 25 | 25 | 50 |
| Pem-2251 L | 1.565 | 6.25 | 12.5 |
| Pem-2252 C | >50 | >50 | >50 |
| Pem-2252 L | 25 | 25 | 25 |
| Pem-2253 C | 50 | 50 | 50 |
| Pem-2253 L | 12.5 | 12.5 | 12.5 |
| Pem-2254 C | 25 | 25 | 50 |
| Pem-2254 L | 1.565 | 1.565 | 3.125 |

For Pem-2251 L and Pem-2254 L peptides, having higher antimicrobial activity as shown in table 2, the MIC values were then tested in 1×PBS against various strains such as Bacillus substilis, Staphylococcus epidermidis, Staphylococcus aureus, Bacillus pumilus, Bacillus cereus, Pseudomonas aeruginosa and E. coli, respectively. The MIC values against various strains are shown in table 3, Pem-2251 L and Pem-2254 L have great microbial activity as well.

TABLE 3

| | MIC (µg/ml) | |
|---|---|---|
| Strains | Pem-2251 L | Pem-2254 L |
| B. substilis | 3.125 | 3.125 |
| S. epidermidis | 3.125 | 1.565 |
| S. aureus | 3.125 | 1.565 |
| B. pumilus | 6.25 | 3.125 |
| B. cereus | 6.25 | 6.25 |
| P. aeruginosa | 6.25 | 3.125 |
| E. coli | 3.125 | 1.565 |

Embodiment 3

Membrane Permeabilization Assays

The outer membrane permeabilization activity of the peptide variants was determined by the 1-N-phenylnaphthylamine (NPN) uptake assay, using intact cells of E. coli. NPN exhibits weak fluorescence in an aqueous environment but exhibits strong fluorescence in a hydrophobic environment. Since NPN is hydrophobic, it provides a direct measurement of the degree of outer membrane permeability. E. coli take up little or no NPN in a general condition. In the presence of permeabilizer compounds (EDTA, polymyxin B, Neomycin, or antimicrobial peptides), NPN partitioned into the bacterial outer membrane resulted in an increase in fluorescence. Fluorescence would vary with the concentration of peptide. The steps of the embodiment were described as follow. One ml of overnight culture was used to inoculate 50 ml of media and incubated at 37° C. with shaking. The culture was permitted to grow to an $OD_{600}$ of 0.4 to 0.6, cells were spun down at 3500 rpm for 10 minutes, washed, and re-suspended in buffer to an $OD_{600}$ of 0.5. The $OD_{600}$ was recorded, 1 ml of cells ($OD_{600}$=0.5) was added to the cuvette and measured after 2-5 seconds. 20 µl NPN 0.5 mM, shaken to mix, was added and measured after 2-5 seconds. 10 ul antibiotic 100× desired final concentration was added, shaken to mix, and measured until the maximal value was reached within 1 to 5 minutes. The concentration of peptide leading to 50% of the maximum increase in NPN uptake was recorded as the $P_{50}$. As results shown in table 4, all of the peptides were capable of interacting with membrane.

TABLE 4

Ability to permeablize and promote NPN uptake across outer membrane of E. coli

| peptide | $P_{50}$ (µg/ml) |
|---|---|
| Pem-1001 L | 6.25 |
| Pem-2251 L | 6.25 |

Embodiment 4

Hemolytic Assay

Melittin, Pem-2252 L and Pem-2254 L were tested for hemolysis against human red blood cells (hRBC). Melittin is a peptide extracted from bees and possesses high hemolytic activity for erythrocytes and used as an experiment control herein. The hRBCs with EDTA were rinsed 3 times with PBS (800×g, 10 min) and re-suspended in PBS. The hRBCs were diluted into 10% with phosphate-buffered saline and placed 50 µl into each eppendorf. The peptides dissolved in PBS were then added to 50 µl of 10% solution of hRBCs and incubated for an hour at 37° C. (final hRBC concentration, 5% v/v). The samples were centrifuged at 800 g for 10 min at $OD_{405}$. Various concentrations of peptides were incubated with pretreated hRBC and the percentage of hemolysis determined (Percentage lysis, Zero hemolysis (blank) and 100% hemolysis were determined in PBS buffer and 1% Triton X-100). As the results shown in table 5 and FIG. 1, Pem-2252 was less hemolytic against hRBC than other antimicrobial peptides. At 5 µg/ml, 50 µg/ml and 400 µg/ml, its lysis percentages were 0.45%, 1.52% and 16.35%, respectively.

TABLE 5

| | lysis percentage (%) | | |
|---|---|---|---|
| peptide name | 5 µg/ml | 50 µg/ml | 400 µg/ml |
| Melittin | 50 | 100 | 100 |
| Pem-2252 L | 3.12 | 9.82 | 37.66 |
| Pem-2254 L | 0.45 | 1.52 | 16.35 |

With reference to the above embodiments, the peptides of the present invention may improve the activity or toxicity of nature antimicrobial peptides. In the future, they can be used to manufacture antibiotics, pharmaceutical composition or for other clinical antimicrobial uses. Through their outstanding antimicrobial effect and low hemolytic activity, these peptides may broadly resist microorganisms such as gram-positive bacteria, gram-negative bacteria, protozoa, fungi or viruses.

The antimicrobial peptide of the present invention and pharmaceutically acceptable carrier can be used to manufacture pharmaceutical composition as antimicrobial agent. The carrier is an excipient, diluent, thickening agent, bulking agent, binder, disintegrating agent, lubricant, oil-based/non-oil-based agent, surfactant, suspending agent, gelling agent, adjuvant, preservative agent, anti-oxidant, stabilizing agent, coloring agent, or flavoring agent. The dosage form of the pharmaceutical composition is an embedding, dip, infusion, patch, powder, tablet, injection, suspension, external aqueous solution, drop, liniment, inhalant, embrocation, paste, lotion, cream, ointment, or gel. The composition can be administered to mammals by means of oral, subcutaneous, injective or inhalation administration.

Although the present invention has been described with reference to the preferred embodiments thereof, it is apparent to those skilled in the art that a variety of modifications and changes may be made without departing from the scope of the present invention which is intended to be defined by the appended claims.

What is claimed is:

1. An antimicrobial peptide, wherein the antimicrobial peptide is selected from the group consisting of SEQ ID NO: 7 to 14.

2. The antimicrobial peptide of claim 1 wherein the peptide is a linear chain peptide.

3. The antimicrobial peptide of claim 1 wherein the peptide is a cyclic peptide.

4. A method comprising the step of administering an antimicrobial peptide to individuals; said peptide is selected from the group consisting of SEQ ID NO: 7 to 14.

5. The method of claim 4, wherein the antimicrobial peptide has low hemolytic activity for the erythrocytes in the individuals.

6. The method of claim 4 wherein the step of administering the antimicrobial peptide is for treating gram-positive bacterial and gram-negative bacterial infections.

7. The method of claim 4 wherein said individuals are animals.

8. The method of claim 4 wherein the antimicrobial peptide is administered orally, subcutaneously, via injection, or via inhalation.

9. A pharmaceutical composition comprising a pharmaceutically acceptable carrier, and an antimicrobial peptide, wherein the antimicrobial peptide is selected from the group consisting of SEQ ID NO: 7 to 14.

10. The pharmaceutical composition of claim 9, wherein the carrier is selected from the group consisting of: excipient, diluent, thickening agent, bulking agent, binder, disintegrating agent, lubricant, oil-based/non-oil-based agent, surfactant, suspending agent, gelling agent, adjuvant, preservative agent, anti-oxidant, stabilizing agent, coloring agent, and flavoring agent.

11. The pharmaceutical composition of claim 9, wherein the pharmaceutical composition is a dosage form selected from the group consisting of: embedding, dip, infusion, patch, powder, tablet, injection, suspension, external aqueous solution, drop, liniment, inhalant, embrocation, paste, lotion, cream, ointment, and gel.

* * * * *

```
                         SEQUENCE LISTING

<160> NUMBER OF SEQ ID NOS: 14

<210> SEQ ID NO 1
<211> LENGTH: 7
<212> TYPE: PRT
<213> ORGANISM: Artificial Sequence
<220> FEATURE:
<223> OTHER INFORMATION: Cyclic topology; cyclic peptides herein were
      synthesized by solid-phase peptide synthesis using the standard
      Fmoc (N-(9-fluoroenyl)methoxycarbonyl) protocol manually on PAL
      resin.

<400> SEQUENCE: 1

Lys Phe Lys Arg Trp Leu Ala
1               5

<210> SEQ ID NO 2
<211> LENGTH: 7
<212> TYPE: PRT
<213> ORGANISM: Artificial Sequence
<220> FEATURE:
<223> OTHER INFORMATION: Linear topology; linear peptides herein were
      synthesized by solid-phase peptide synthesis using the standard
      Fmoc (N-(9-fluoroenyl)methoxycarbonyl) protocol manually on PAL
      resin.

<400> SEQUENCE: 2

Lys Phe Lys Arg Trp Leu Ala
1               5

<210> SEQ ID NO 3
<211> LENGTH: 7
<212> TYPE: PRT
<213> ORGANISM: Artificial Sequence
<220> FEATURE:
<223> OTHER INFORMATION: Cyclic topology; cyclic peptides herein were
      synthesized by solid-phase peptide synthesis using the standard
      Fmoc (N-(9-fluoroenyl)methoxycarbonyl) protocol manually on PAL
      resin.

<400> SEQUENCE: 3

Lys Phe Arg Ala Trp Val Arg
1               5

<210> SEQ ID NO 4
<211> LENGTH: 7
<212> TYPE: PRT
<213> ORGANISM: Artificial Sequence
<220> FEATURE:
<223> OTHER INFORMATION: Linear topology; linear peptides herein were
      synthesized by solid-phase peptide synthesis using the standard
      Fmoc (N-(9-fluoroenyl)methoxycarbonyl) protocol manually on PAL
      resin.

<400> SEQUENCE: 4

Lys Phe Arg Ala Trp Val Arg
1               5

<210> SEQ ID NO 5
<211> LENGTH: 7
<212> TYPE: PRT
<213> ORGANISM: Artificial Sequence
```

```
<220> FEATURE:
<223> OTHER INFORMATION: Cyclic topology; cyclic peptides herein were
      synthesized by solid-phase peptide synthesis using the standard
      Fmoc (N-(9-fluoroenyl)methoxycarbonyl) protocol manually on PAL
      resin.

<400> SEQUENCE: 5

Lys Trp Lys Ile Trp Leu Lys
1               5

<210> SEQ ID NO 6
<211> LENGTH: 7
<212> TYPE: PRT
<213> ORGANISM: Artificial Sequence
<220> FEATURE:
<223> OTHER INFORMATION: Linear topology; linear peptides herein were
      synthesized by solid-phase peptide synthesis using the standard
      Fmoc (N-(9-fluoroenyl)methoxycarbonyl) protocol manually on PAL
      resin.

<400> SEQUENCE: 6

Lys Trp Lys Ile Trp Leu Lys
1               5

<210> SEQ ID NO 7
<211> LENGTH: 13
<212> TYPE: PRT
<213> ORGANISM: Artificial Sequence
<220> FEATURE:
<223> OTHER INFORMATION: Cyclic topology; cyclic peptides herein were
      synthesized by solid-phase peptide synthesis using the standard
      Fmoc (N-(9-fluoroenyl)methoxycarbonyl) protocol manually on PAL
      resin.

<400> SEQUENCE: 7

Lys Lys Trp Arg Ala Trp Leu Lys Trp Leu Ala Lys Lys
1               5                   10

<210> SEQ ID NO 8
<211> LENGTH: 13
<212> TYPE: PRT
<213> ORGANISM: Artificial Sequence
<220> FEATURE:
<223> OTHER INFORMATION: Linear topology; linear peptides herein were
      synthesized by solid-phase peptide synthesis using the standard
      Fmoc (N-(9-fluoroenyl)methoxycarbonyl) protocol manually on PAL
      resin.

<400> SEQUENCE: 8

Lys Lys Trp Arg Ala Trp Leu Lys Trp Leu Ala Lys Lys
1               5                   10

<210> SEQ ID NO 9
<211> LENGTH: 13
<212> TYPE: PRT
<213> ORGANISM: Artificial Sequence
<220> FEATURE:
<223> OTHER INFORMATION: Cyclic topology; cyclic peptides herein were
      synthesized by solid-phase peptide synthesis using the standard
      Fmoc (N-(9-fluoroenyl)methoxycarbonyl) protocol manually on PAL
      resin.

<400> SEQUENCE: 9

Lys Lys Trp Arg Lys Trp Leu Arg Ala Ile Ala Lys Lys
1               5                   10
```

```
<210> SEQ ID NO 10
<211> LENGTH: 13
<212> TYPE: PRT
<213> ORGANISM: Artificial Sequence
<220> FEATURE:
<223> OTHER INFORMATION: Linear topology; linear peptides herein were
      synthesized by solid-phase peptide synthesis using the standard
      Fmoc (N-(9-fluoroenyl)methoxycarbonyl) protocol manually on PAL
      resin.

<400> SEQUENCE: 10

Lys Lys Trp Arg Lys Trp Leu Arg Ala Ile Ala Lys Lys
1               5                   10

<210> SEQ ID NO 11
<211> LENGTH: 13
<212> TYPE: PRT
<213> ORGANISM: Artificial Sequence
<220> FEATURE:
<223> OTHER INFORMATION: Cyclic topology; cyclic peptides herein were
      synthesized by solid-phase peptide synthesis using the standard
      Fmoc (N-(9-fluoroenyl)methoxycarbonyl) protocol manually on PAL
      resin.

<400> SEQUENCE: 11

Lys Lys Phe Arg Arg Phe Val Arg Phe Ile Ala Lys Lys
1               5                   10

<210> SEQ ID NO 12
<211> LENGTH: 13
<212> TYPE: PRT
<213> ORGANISM: Artificial Sequence
<220> FEATURE:
<223> OTHER INFORMATION: Linear topology; linear peptides herein were
      synthesized by solid-phase peptide synthesis using the standard
      Fmoc (N-(9-fluoroenyl)methoxycarbonyl) protocol manually on PAL
      resin.

<400> SEQUENCE: 12

Lys Lys Phe Arg Arg Phe Val Arg Phe Ile Ala Lys Lys
1               5                   10

<210> SEQ ID NO 13
<211> LENGTH: 13
<212> TYPE: PRT
<213> ORGANISM: Artificial Sequence
<220> FEATURE:
<223> OTHER INFORMATION: Cyclic topology; cyclic peptides herein were
      synthesized by solid-phase peptide synthesis using the standard
      Fmoc (N-(9-fluoroenyl)methoxycarbonyl) protocol manually on PAL
      resin.

<400> SEQUENCE: 13

Lys Lys Trp Arg Lys Trp Leu Lys Trp Leu Ala Lys Lys
1               5                   10

<210> SEQ ID NO 14
<211> LENGTH: 13
<212> TYPE: PRT
<213> ORGANISM: Artificial Sequence
<220> FEATURE:
<223> OTHER INFORMATION: Linear topology; linear peptides herein were
      synthesized by solid-phase peptide synthesis using the standard
      Fmoc (N-(9-fluoroenyl)methoxycarbonyl) protocol manually on PAL
      resin.

<400> SEQUENCE: 14

Lys Lys Trp Arg Lys Trp Leu Lys Trp Leu Ala Lys Lys
1               5                   10
```